(12) United States Patent
Heiliger (10) Patent No.: US 11,969,203 B2
(45) Date of Patent: Apr. 30, 2024

(54) COLPOTOMY SYSTEM WITH APPLIED ENERGY

(71) Applicant: Covidien LP, Mansfield, MA (US)

(72) Inventor: Zachary S. Heiliger, Nederland, CO (US)

(73) Assignee: Covidien LP, Mansfield, MA (US)

( * ) Notice: Subject to any disclaimer, the term of this patent is extended or adjusted under 35 U.S.C. 154(b) by 500 days.

(21) Appl. No.: 17/173,678

(22) Filed: Feb. 11, 2021

(65) Prior Publication Data

US 2021/0251685 A1 Aug. 19, 2021

Related U.S. Application Data (60) Provisional application No. 62/976,602, filed on Feb. 14, 2020.

(51) Int. Cl.
| | | |
|---|---|---|
| *A61B 18/12* | (2006.01) | |
| *A61B 17/42* | (2006.01) | |
| *A61B 18/14* | (2006.01) | |
| *A61B 18/00* | (2006.01) | |

(52) U.S. Cl.
CPC ...... *A61B 18/1445* (2013.01); *A61B 17/4241* (2013.01); *A61B 18/1206* (2013.01); *A61B 2018/00559* (2013.01); *A61B 2018/1455* (2013.01)

(58) Field of Classification Search
CPC ........... A61B 18/1206; A61B 18/1442; A61B 18/1445; A61B 18/1485; A61B 2018/00559; A61B 2018/00607; A61B 2018/0063; A61B 2018/1455
See application file for complete search history.

(56) References Cited

U.S. PATENT DOCUMENTS

| | | |
|---|---|---|
| 4,597,030 A | 6/1986 | Brody et al. |
| 4,804,240 A | 2/1989 | Mori |
| 5,209,754 A | 5/1993 | Ahluwalia |
| 5,394,863 A | 3/1995 | Sanford et al. |
| 5,451,221 A | 9/1995 | Cho et al. |
| 5,487,377 A | 1/1996 | Smith et al. |
| 5,520,698 A | 5/1996 | Koh |
| 5,643,285 A | 7/1997 | Rowden et al. |
| 5,840,077 A | 11/1998 | Rowden et al. |
| 6,129,662 A | 10/2000 | Li et al. |
| 6,423,075 B1 | 7/2002 | Singh et al. |
| 6,516,216 B1 | 2/2003 | Fontenot et al. |
| 8,025,670 B2 | 9/2011 | Sharp et al. |

(Continued)

FOREIGN PATENT DOCUMENTS

| | | |
|---|---|---|
| CN | 202489982 U | 10/2012 |
| CN | 202920313 U | 5/2013 |

(Continued)

*Primary Examiner* — Daniel W Fowler
(74) *Attorney, Agent, or Firm* — Carter, DeLuca & Farrell LLP (57) ABSTRACT

A colpotomy system includes a surgical instrument and a uterine manipulator. The surgical instrument has a shaft assembly. The shaft assembly includes an end effector supported on a distal end portion of the shaft assembly. The end effector includes a first jaw member and a second jaw member. The uterine manipulator extends distally to a head supporting a knife that is positioned to cooperate with the first and second jaw members of the end effector.

12 Claims, 9 Drawing Sheets

(56) References Cited

U.S. PATENT DOCUMENTS

| | | |
|---|---|---|
| 8,128,622 B2 | 3/2012 | Podhajsky et al. |
| 8,192,444 B2 | 6/2012 | Dycus |
| 8,206,357 B2 | 6/2012 | Bettuchi |
| 8,292,901 B2 | 10/2012 | Auerbach et al. |
| 8,298,213 B2 | 10/2012 | Singh |
| 8,323,278 B2 | 12/2012 | Brecheen et al. |
| 8,453,910 B2 | 6/2013 | Bettuchi et al. |
| 8,460,289 B2 | 6/2013 | Sartor |
| 8,528,563 B2 | 9/2013 | Gruber |
| 8,545,513 B2 | 10/2013 | Blair et al. |
| 8,603,105 B2 | 12/2013 | Sauer |
| 8,663,239 B2 | 3/2014 | Hess |
| 8,696,563 B2 | 4/2014 | Williams et al. |
| 8,784,410 B2 | 7/2014 | Dunning |
| 8,939,988 B2 | 1/2015 | Auerbach et al. |
| 9,011,433 B2 | 4/2015 | Batchelor et al. |
| 9,022,927 B2 | 5/2015 | Kleyman |
| 9,033,977 B2 | 5/2015 | Morozov |
| 9,066,724 B2 | 6/2015 | Jenkins |
| 9,101,390 B2 | 8/2015 | Singh et al. |
| 9,144,454 B2 | 9/2015 | Batchelor et al. |
| 9,392,935 B2 | 7/2016 | Adams et al. |
| 9,655,673 B2 | 5/2017 | McCullough, Jr. et al. |
| 9,820,765 B2 | 11/2017 | Allen, IV et al. |
| 2003/0187334 A1 | 10/2003 | Biswas |
| 2005/0085827 A1 | 4/2005 | G. et al. |
| 2005/0125006 A1* | 6/2005 | Nady ................ A61B 17/42 606/119 |
| 2006/0271037 A1 | 11/2006 | Maroney et al. |
| 2006/0291195 A1 | 12/2006 | Horrell et al. |
| 2007/0142844 A1* | 6/2007 | Kotmel ............... A61B 17/42 606/119 |
| 2008/0208210 A1 | 8/2008 | Blair et al. |
| 2010/0280524 A1 | 11/2010 | Lopez Zepeda |
| 2011/0130769 A1 | 6/2011 | Boebel et al. |
| 2011/0190689 A1 | 8/2011 | Bennett et al. |
| 2012/0016185 A1 | 1/2012 | Sherts et al. |
| 2012/0116416 A1 | 5/2012 | Neff et al. |
| 2012/0143210 A1 | 6/2012 | Brecheen et al. |
| 2012/0165826 A1 | 6/2012 | Rhemrev-Pieters |
| 2012/0283718 A1 | 11/2012 | Cosmescu |
| 2012/0323079 A1 | 12/2012 | Bakare et al. |
| 2012/0330324 A1 | 12/2012 | Sauer |
| 2013/0066328 A1 | 3/2013 | Singh et al. |
| 2013/0085508 A1 | 4/2013 | Hess |
| 2013/0110126 A1 | 5/2013 | Mujwid |
| 2013/0131459 A1 | 5/2013 | Williams et al. |
| 2014/0012305 A1 | 1/2014 | Horton et al. |
| 2014/0194875 A1* | 7/2014 | Reschke ............ A61B 18/1445 606/45 |
| 2014/0303641 A1 | 10/2014 | Boebel et al. |
| 2014/0358158 A1 | 12/2014 | Einarsson |
| 2015/0005780 A1 | 1/2015 | Einarsson |
| 2015/0080905 A1 | 3/2015 | Begemann et al. |
| 2015/0127016 A1 | 5/2015 | Sauer |
| 2015/0351621 A1 | 12/2015 | Hill et al. |
| 2016/0045757 A1 | 2/2016 | Groseth |
| 2016/0074186 A1 | 3/2016 | Sartor et al. |
| 2016/0095649 A1 | 4/2016 | Motai et al. |
| 2016/0100861 A1 | 4/2016 | Parys et al. |
| 2016/0100862 A1 | 4/2016 | Parys |
| 2016/0106463 A1 | 4/2016 | Egle et al. |
| 2016/0262826 A1* | 9/2016 | Allen, IV ............ A61B 17/295 |
| 2018/0325552 A1* | 11/2018 | Weihe ................ A61B 18/1482 |

FOREIGN PATENT DOCUMENTS

| | | |
|---|---|---|
| CN | 203244440 U | 10/2013 |
| CN | 203303125 U | 11/2013 |
| CN | 204446045 U | 7/2015 |
| CN | 204698659 U | 10/2015 |
| CN | 205072992 U | 3/2016 |
| DE | 102009018521 A1 | 10/2010 |
| EP | 0865760 A1 | 9/1998 |
| EP | 2243437 A1 | 10/2010 |
| WO | 03015643 A2 | 2/2003 |
| WO | 2008136024 A1 | 11/2008 |
| WO | 2011140604 A1 | 11/2011 |
| WO | 2012151622 A1 | 11/2012 |
| WO | 2013090909 A1 | 6/2013 |
| WO | 2016025132 A1 | 2/2016 |

* cited by examiner

COLPOTOMY SYSTEM WITH APPLIED ENERGY

CROSS REFERENCE TO RELATED APPLICATIONS

This application claims the benefit of U.S. Provisional Application Ser. No. 62/976,602, filed Feb. 14, 2020, the entire contents of which are incorporated by reference herein.

TECHNICAL FIELD

This disclosure relates to hysterectomy and, more particularly, to systems for performing a colpotomy procedure.

BACKGROUND

Colpotomy, one of the final steps in a hysterectomy, requires making a circular incision in vaginal tissue to separate the uterus from the vagina with a cutting tool such as a surgical electrode instrument. This incision is typically performed with the aid of a uterine manipulator. Uterine manipulators are conventionally used during laparoscopic hysterectomy procedures to mobilize and position the vagina and the cervix to facilitate separation and to enable removal of the uterus or other tissue specimens subsequent to performance of a colpotomy.

SUMMARY

Accordingly, a need exists to provide systems, devices, and/or methods for improving colpotomy procedures.

In accordance with an aspect of this disclosure, an electrosurgical colpotomy system includes an energy source, an electrosurgical instrument, and a uterine manipulator. The electrosurgical instrument has a shaft assembly including an end effector supported on a distal end portion of the shaft assembly. The end effector is in electrical communication with the energy source. The end effector includes a first jaw member and a second jaw member supporting a first treatment surface. The uterine manipulator has a head including a second treatment surface. The second treatment surface is electrically coupled to the energy source and configured to transmit electrical energy to the first treatment surface when the first and second jaw members are positioned about the head of the uterine manipulator.

In aspects, the first and second jaw members of the end effector may be selectively movable between an open position and a closed position to capture tissue between the head of the uterine manipulator and the end effector of the electrosurgical instrument.

In various aspects, the first treatment surface may include a first seal plate and the second treatment surface may include a second seal plate. The first seal plate and the second seal plate may be configured to conduct electrical energy from the energy source.

In aspects, the head of the uterine manipulator may support a knife assembly having a knife configured to cut tissue adjacent to the second treatment surface. The uterine manipulator may define a longitudinal axis and may include a rotatable actuator that is operable to enable the knife to rotate about the longitudinal axis.

In various aspects, the first jaw member and the second jaw member may have an arcuate profile that cooperate to define a ring when the first jaw member and the second jaw member are disposed in the closed position. The ring may be configured to receive the head of the uterine manipulator.

In some aspects, the first jaw member and the second jaw member may define a blade slot positioned to receive the knife. The blade slot may define an arcuate path through which the knife is configured to pass as the knife rotates relative to the end effector.

In aspects, the energy source may include a generator.

According to one aspect of this disclosure, a method for effectuating a colpotomy is provided. The method includes positioning a head of a uterine manipulator adjacent to a uterus of a patient, positioning an end effector of an electrosurgical instrument adjacent to the head of the uterine manipulator to capture tissue of the patient between the end effector of the electrosurgical instrument and the head of the uterine manipulator, transmitting electrical energy to the head of the uterine manipulator and to the end effector of the electrosurgical instrument to treat the tissue captured between the end effector of the electrosurgical instrument and the head of the uterine manipulator, and rotating a knife through the end effector of the electrosurgical instrument to effectuate a colpotomy on the uterus.

In aspects, rotating the knife through the end effector of the electrosurgical instrument to effectuate the colpotomy on the uterus may include rotating the uterine manipulator relative to the end effector.

In some aspects, the method may further comprise receiving the knife through a blade slot defined in the end effector.

In various aspects, the method may further comprise pivoting a first jaw member and a second jaw member of the end effector of the electrosurgical instrument between an open position and a closed position to capture the tissue on the head of the uterine manipulator.

According to yet another aspect, a colpotomy system includes a surgical instrument and a uterine manipulator. The surgical instrument has a shaft assembly. The shaft assembly includes an end effector supported on a distal end portion of the shaft assembly. The end effector includes a first jaw member and a second jaw member. The uterine manipulator extends distally to a head supporting a knife that is positioned to cooperate with the first and second jaw members of the end effector.

In aspects, the first and second jaw members may be selectively movable between an open position and a closed position to capture tissue between the head of the uterine manipulator and the end effector.

In various aspects, the uterine manipulator may include a rotatable actuator operatively coupled to the knife. The rotatable actuator may be operable to rotate the knife relative to the end effector of the electrosurgical instrument.

In aspects, the first jaw member and the second jaw member may have an arcuate profile that defines a ring when the first jaw member and the second jaw member are disposed in the closed position.

In aspects, the first jaw member and the second jaw member may define a blade slot positioned to receive the knife therein as the knife rotates relative to the end effector.

In some aspects, the uterine manipulator and the surgical instrument may be coupled to a generator.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate aspects of this disclosure and, together with a general description of this disclosure given above, and the detailed description given below, serve to explain the principles of this disclosure, wherein.

DETAILED DESCRIPTION

Aspects of this disclosure are described in detail with reference to the drawings, in which like reference numerals designate identical or corresponding elements in each of the several views. As used herein, the term "distal" refers to that portion of structure farther from the user, while the term "proximal" refers to that portion of structure, closer to the user. As used herein, the term "clinician" refers to a doctor, nurse, or other care provider and may include support personnel.

In the following description, well-known functions or constructions are not described in detail to avoid obscuring the present disclosure in unnecessary detail.

Turning now to FIGS. 1-14, an electrosurgical colpotomy system, generally referred to as 10, is shown. Electrosurgical colpotomy system 10 includes an energy source 100, a uterine manipulator 200, and an electrosurgical instrument 300 that are configured to cooperate to effectuate a colpotomy. In particular, uterine manipulator 200 and electrosurgical instrument 300 are electrically coupled to energy source 100 (e.g., a generator) to selectively treat (e.g., coagulate, seal, etc.) tissue such as vaginal or uterine tissue. For a more detailed description of one example of an energy source such as an electrosurgical generator, reference can be made to U.S. Pat. No. 8,784,410, the entire contents of which are incorporated by reference herein.

Figure 1:
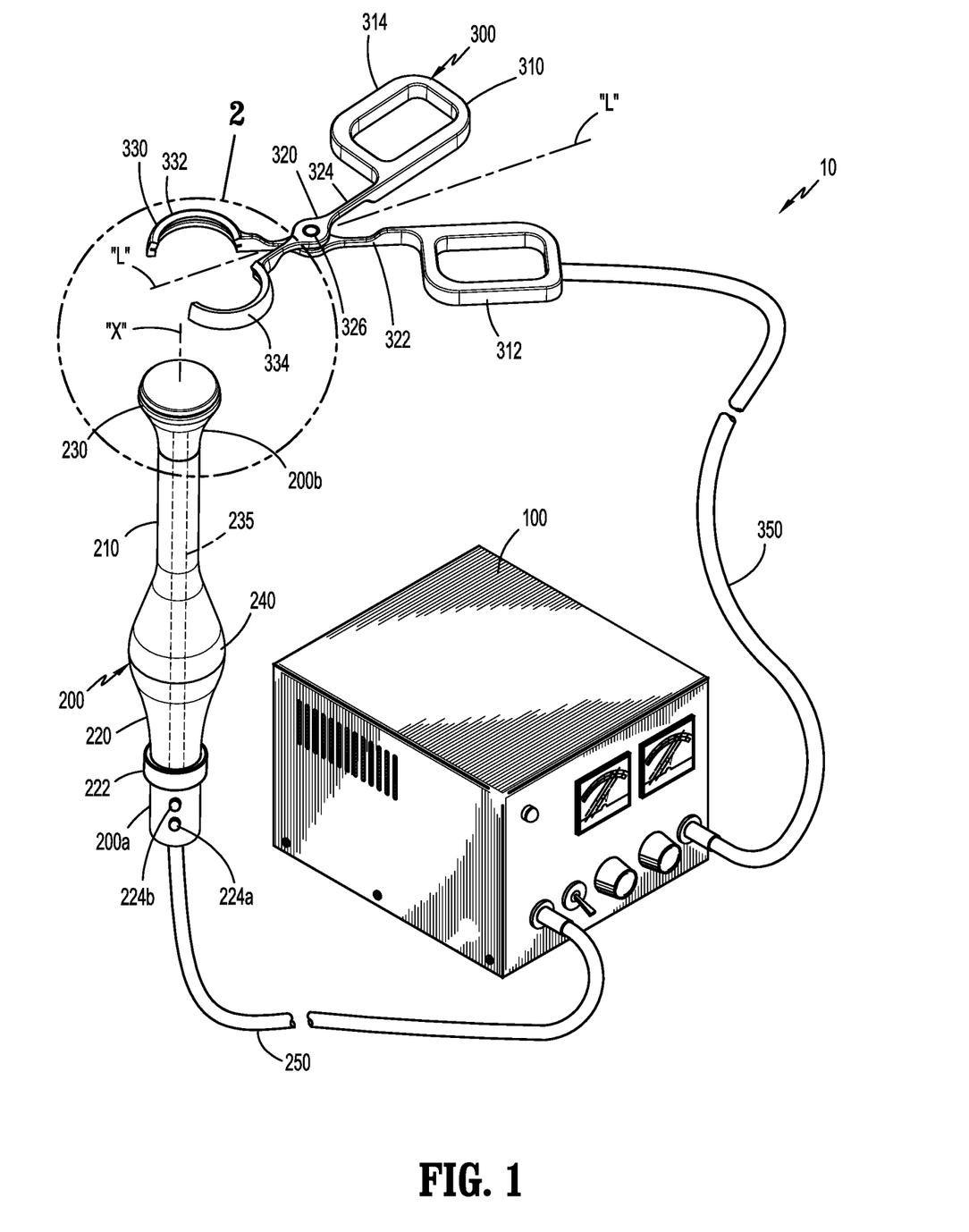
FIG. 1 is a perspective view of a colpotomy system in accordance with the principles of this disclosure.
Figure 3:
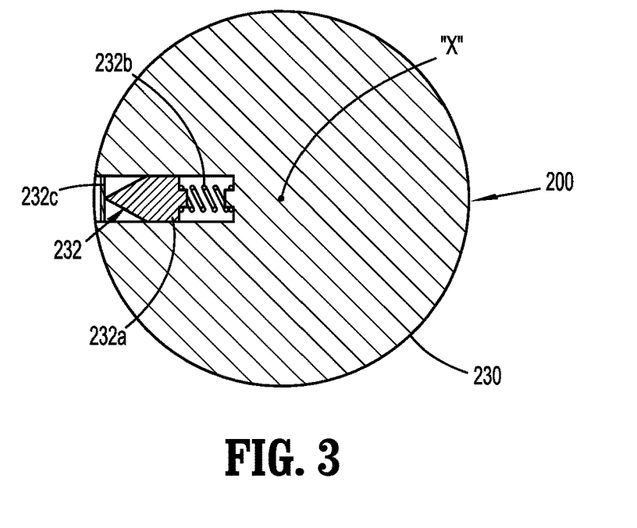
FIG. 3 is an enlarged, cross-sectional view as taken along section line 3-3 of FIG. 2.
Figure 4:
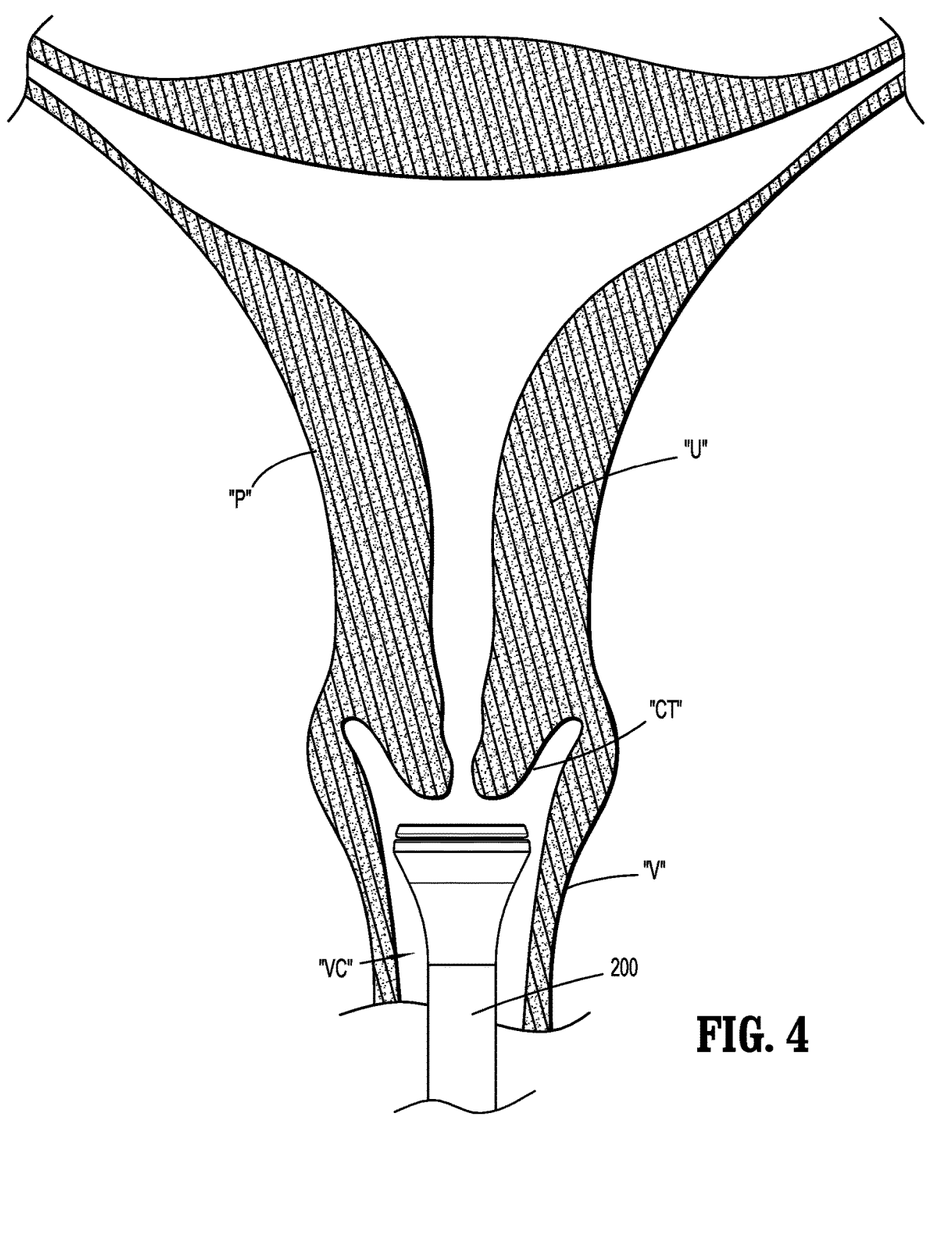
FIGS. 4-14 are progressive views illustrating the colpotomy system of FIG. 1 effectuating a colpotomy.
Figure 5:
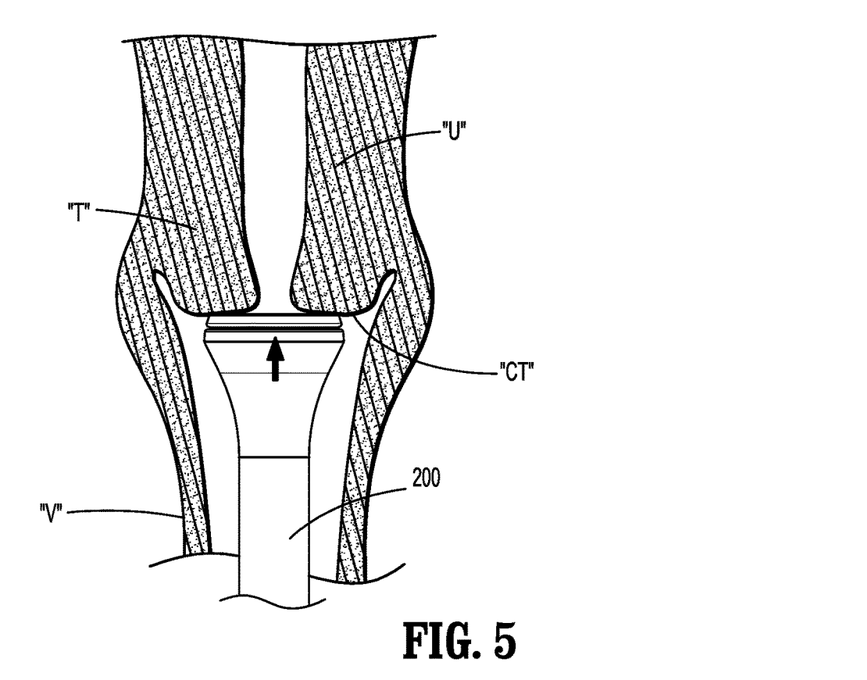
Figure 6:
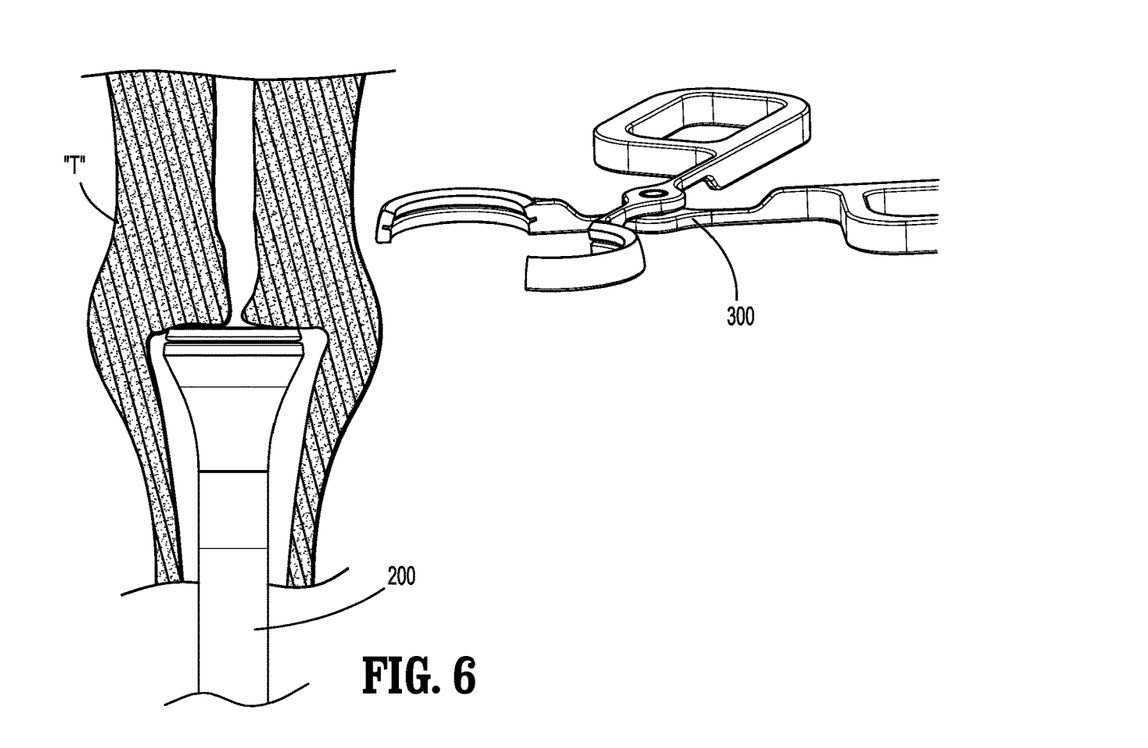
Figure 12:
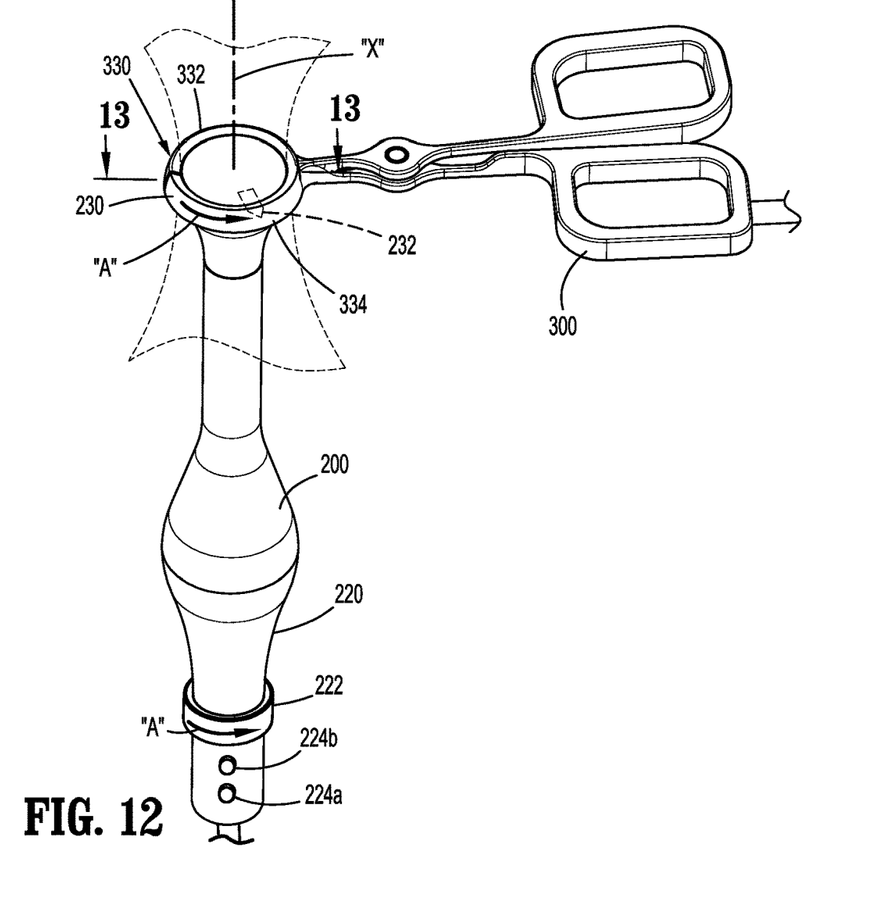
Figure 13:
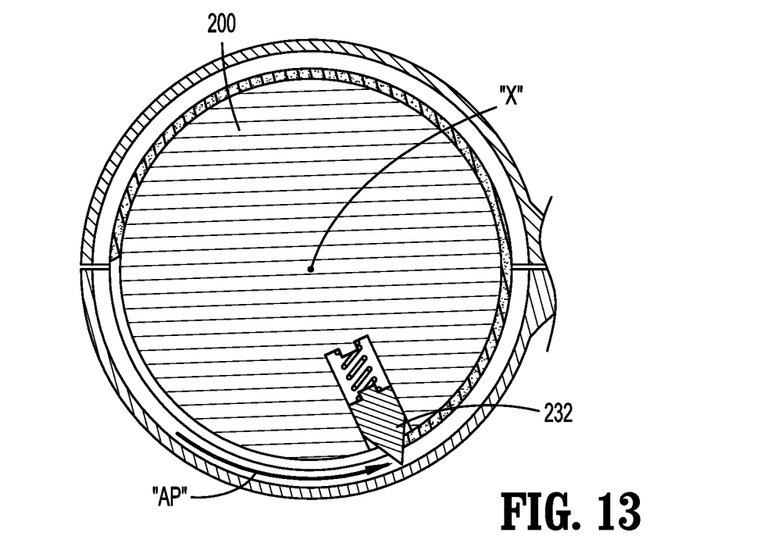

With reference to FIG. 1, uterine manipulator 200 of electrosurgical colpotomy system 10 has a proximal portion 200a and a distal portion 200b that define a longitudinal axis "X" therethrough. Uterine manipulator 200 includes an elongated shaft 210 having a handle portion 220 on a proximal end portion thereof and a head 230 on a distal end portion thereof. As seen in FIG. 3, head 230 supports a knife assembly 232 having a knife 232a that is configured to rotate about longitudinal axis "X" of uterine manipulator 200. With reference again to FIG. 1, uterine manipulator 200 further includes a bulbous portion 240 disposed on the proximal end portion of elongated shaft 210 distal to handle portion 220 to limit insertion depth of head 230 when uterine manipulator 200 is inserted transvaginally. For instance, bulbous portion 240 is positioned to engage tissue adjacent a vaginal opening (not shown) of the patient so that bulbous portion 240 acts as a limit stop for head 230 of uterine manipulator 200, but has an orbicular configuration to prevent tissue damage. Handle portion 220 further includes one or more actuators 224a, 224b, for example, buttons, knobs, switches, etc. for operating uterine manipulator 200 or portions thereof such as head 230. Handle portion 220 also includes a rotatable actuator 222 that is rotatably supported on handle portion 220 (e.g., by one or more bearings—not shown) to rotate a distal portion 200b relative to a proximal portion 200a of uterine manipulator 200. For example, rotation of rotatable actuator 222 about longitudinal axis "X," as indicated by arrows "A," can rotate head 230 relative to handle portion 220 to facilitate cutting with knife assembly 232, as illustrated in FIG. 12.

Referring again to FIG. 3, knife assembly 232 of uterine manipulator 200 further includes a spring 232b supported within head 230 and a retractable door 232c that is operatively coupled to actuator 224a and/or rotatable actuator 222 via a drive assembly 235 (see FIG. 1) supported by uterine manipulator 200 to selectively open and/or close retractable door 232c to selectively enable deployment or retraction of knife 232a relative to head 230. Knife 232a can be retracted to facilitate transvaginal insertion and removal of uterine manipulator 200 without damaging tissue, and deployed to facilitate tissue cutting.

As seen in FIG. 1, uterine manipulator 200 further includes a first cable 250 (e.g., a supply or return line) that extends from proximally from the proximal end portion of handle portion 220 of uterine manipulator 200 for selective connection to energy source 100. Actuator 224b of handle portion 220 can be utilized to cause electrical energy to be transmitted from energy source 100 to uterine manipulator 200.

Figure 2:
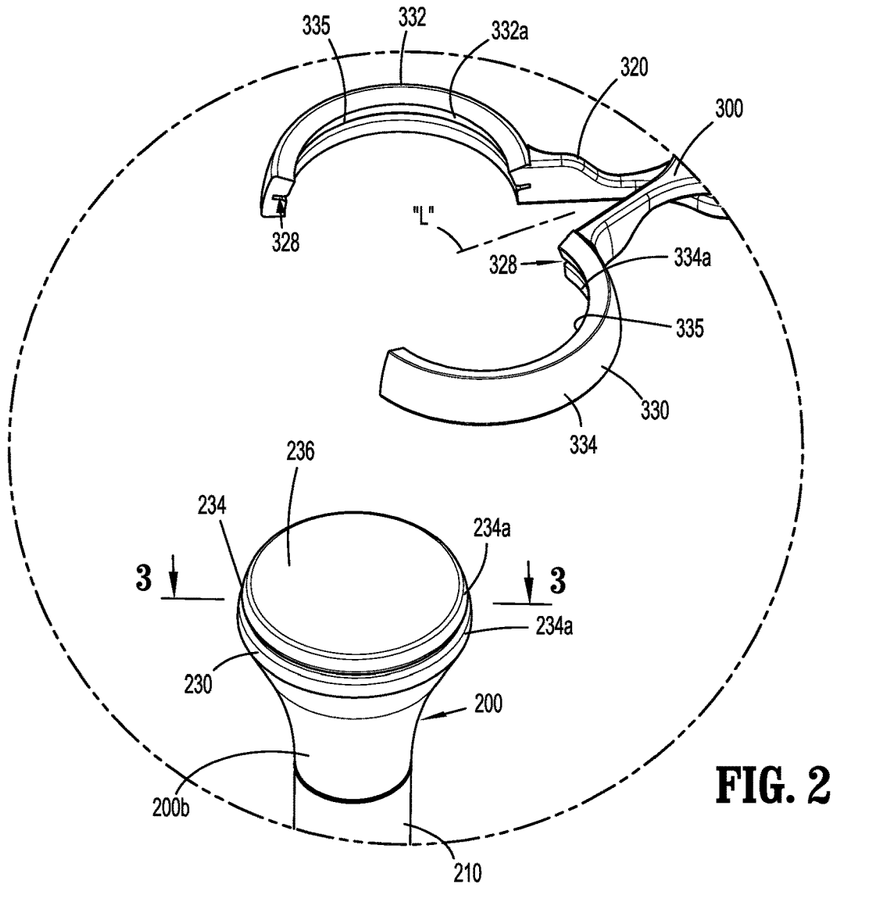
FIG. 2 is an enlarged, perspective view of the indicated area of detail shown in FIG. 1.

With reference to FIGS. 1 and 2, head 230 of uterine manipulator further includes one or more outer treatment surfaces 234 that include electrically conductive material (e.g., metallic material) and which may be electrically isolated from one or more portions of head 230, elongated shaft 210, handle portion 220, and/or bulbous portion 240 of uterine manipulator 200. Treatment surfaces 234 may be have an annular arrangement about an outer side surface of head 230. Treatment surfaces 234 may be in the form of one or more seal plates 234a secured to the outer side surface of head 230 using any known securement technique such as fastening, crimping, snap-fit, friction-fit, adhesive, etc. Head 230 extends to a distal end face 236, which may be planar, to facilitate uterine manipulation. For a more detailed description of a seal plates, or components thereof, which can be included or modified for inclusion in electrosurgical instrument 200, reference can be made, for example, to U.S. Pat. No. 9,655,673 to McCullough, Jr. et al. and U.S. Pat. No. 9,820,765 to Allen et al., the entire contents of each of which are incorporated herein by reference.

Electrosurgical instrument 300 of electrosurgical colpotomy system 10 defines a longitudinal axis "L" and includes a handle assembly 310 on a proximal end portion thereof that extends distally to a shaft assembly 320. Shaft assembly 320 of electrosurgical instrument 300 includes an end effector 330 supported on a distal end portion thereof. Handle assembly 310 includes a first handle 312 and a second handle 314 that are each configured for finger grasping and manipulation. Handle assembly 310 further includes a second cable 350 (e.g., a supply or return line) that extends from proximally from the proximal end portion of handle assembly 310 for selective connection to energy source 100. End effector 330 of electrosurgical instrument 300 includes a first jaw member 332 and a second jaw member 334, each of which may have a curved or arcuate profile (e.g., crescent-shaped). First and second jaw members 332, 334 may be mirror images of one another. Shaft assembly 320 of electrosurgical instrument 300 includes a first shaft 322 and a second shaft 324 that are pivotably coupled together at a pivot 326 (e.g., a pivot pin transverse to longitudinal axis "L") to facilitate pivoting movement of first and second jaw members 332, 334 relative to one another and longitudinal axis "L." First shaft 322 supports first jaw member 332 of end effector 330 on a distal end portion thereof and first handle 312 of handle assembly 310 on a proximal end portion thereof. Second shaft 324 supports second jaw member 334 of end effector 330 on a distal end portion thereof and second handle 314 of handle assembly 310 on a proximal end portion thereof. First and second jaw members 332, 334 are movable relative to one another between an open position (see FIGS. 1 and 2) and a closed position (see FIGS. 7 and 12) as first and second shafts 322, 324 pivot about pivot 326 in response to movement of first and second handles 312, 314 relative to one another (e.g., scissor-like movement).

Figure 7:
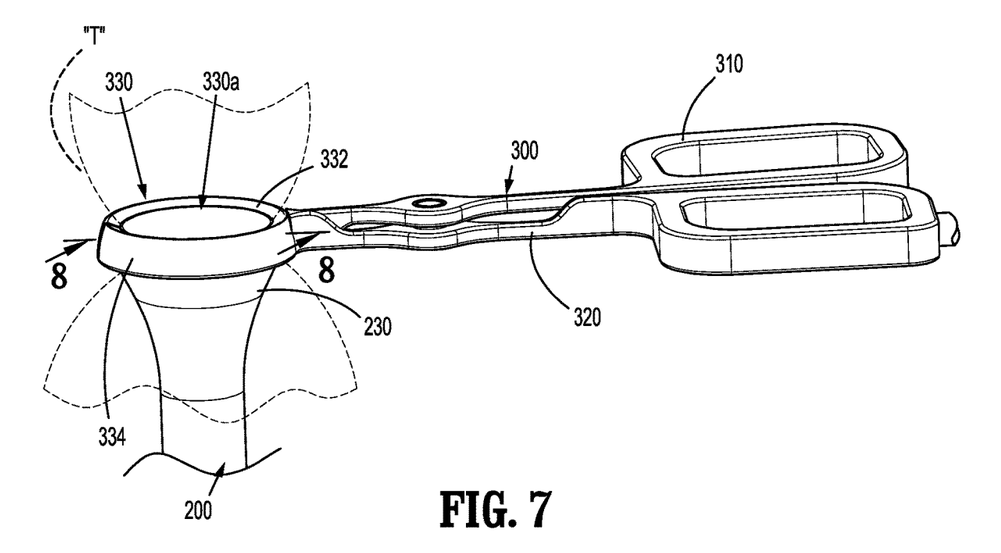
Figure 8:
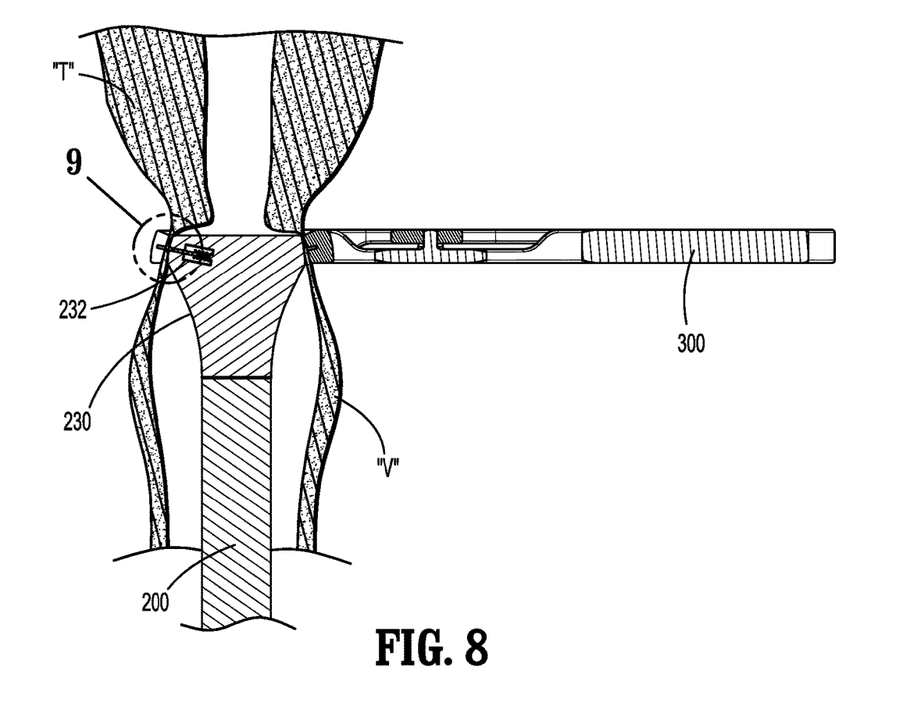
Figure 9:
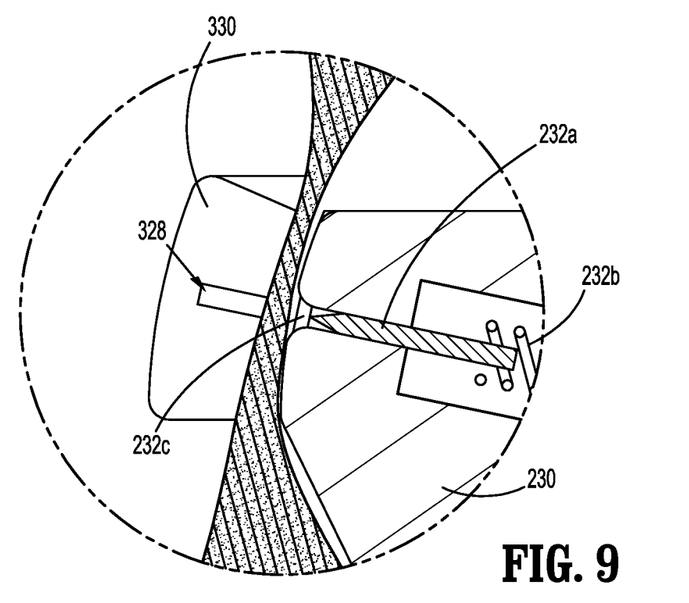
Figure 10:
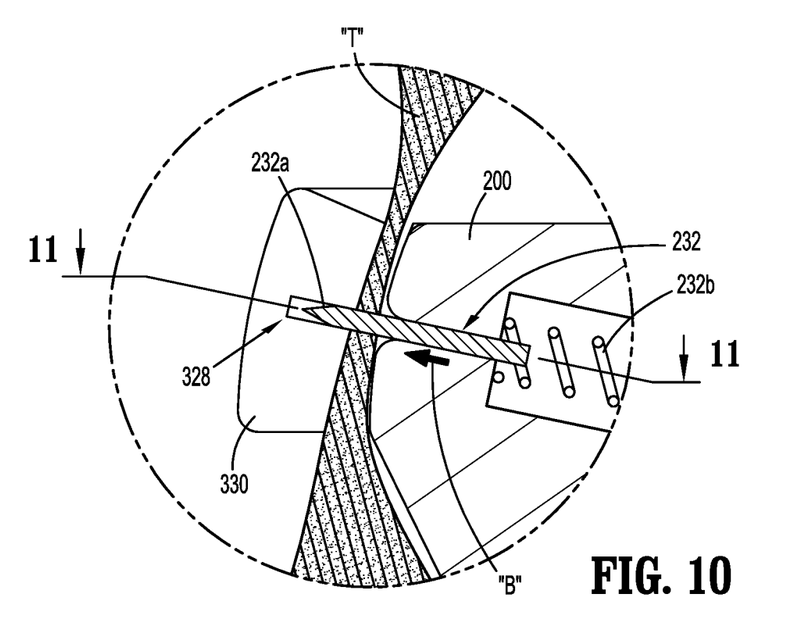
Figure 11:
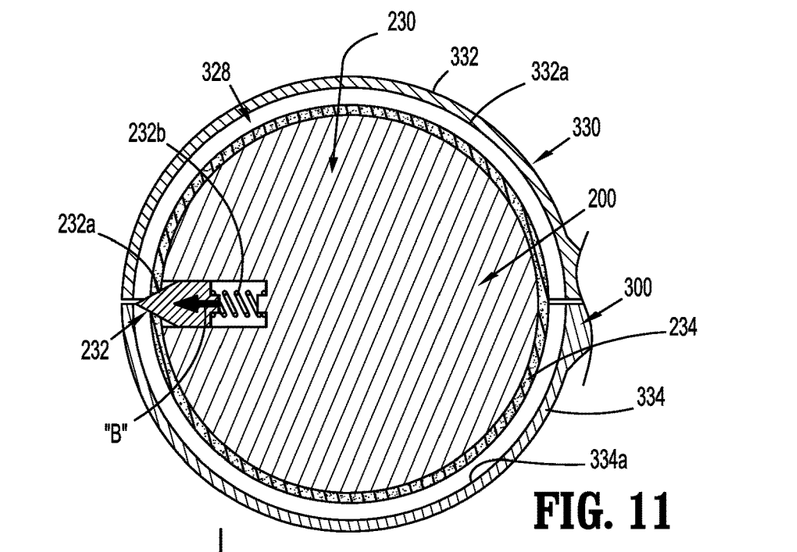

As seen in FIG. 7, in the closed position, first and second jaw members 332, 334 of end effector 330 cooperate to define a ring with an annular opening 330a therethrough for receiving a distal portion of head 230 of uterine manipulator 200 and tissue "T" therein. With reference also to FIG. 2, first and second jaw members 332, 334 include inner treatment surfaces 332a, 334a that include electrically conductive material (e.g., metallic), and which may be electrically isolated from one or more portions of end effector 330, shaft assembly 320, and/or handle assembly 310 of electrosurgical instrument 300. Treatment surfaces 332a, 334a may be in the form of one or more seal plates 335. Treatment surfaces 332a, 334a are configured to cooperate with treatment surfaces 234 of uterine manipulator 200 to conduct electrical energy. In some aspects of this disclosure, electrical energy may be conducted between treatment surfaces of uterine manipulator 200 and electrosurgical instrument 300 to treat tissue captured between end effector 330 of electrosurgical instrument 300 and head 230 of uterine manipulator 200 as illustrated in FIG. 7. First and second jaw members 332, 324 further include a blade slot 328 defined therein to enable knife 232a of knife assembly 232 of uterine manipulator 200 to pass therethrough as knife 232a rotates through an arcuate path "AP" defined by blade slot 328 relative to end effector 330 about longitudinal axis "X" of uterine manipulator 200 (see FIGS. 12 and 13).

With reference to FIGS. 4-14, in use, uterine manipulator 200 is introduced transvaginally (through vaginal canal "VC" of the vagina "V" of the patient "P") and positioned in abutment with tissue such as cervical tissue "CT" to manipulate the tissue "T" and/or uterus "U" as desired to effectuate a colpotomy. In particular, the tissue "T" can be manipulated with the uterine manipulator 200 such that portions of the tissue "T" are arranged along outer side surfaces of head 230 of uterine manipulator 200 (e.g. in contact therewith) and adjacent knife assembly 232 so as to enable knife 232a of knife assembly 232 to deploy into (e.g., through) such adjacent tissue for annularly severing the adjacent tissue to effectuate a colpotomy. Electrosurgical instrument 300 can be introduced, for example, through a separate abdominal incision and/or through a surgical access port or trocar such as 5-12 mm cannulas (not shown). For a more detailed description of one example of a surgical access port, reference can be made to U.S. Pat. No. 9,022, 927 or 8,206,357, the entire contents of each of which are incorporated by reference herein.

With uterine manipulator 200 in a desired position, electrosurgical instrument 300 is positioned so that first and second jaw members 332, 334 can be moved from the open position thereof to the closed position thereof to clamp around the tissue adjacent head 230 of uterine manipulator 200 and onto head 230 of uterine manipulator 200. With end effector 330 of electrosurgical instrument 300 clamped around the tissue and onto head 230 of uterine manipulator 200, blade slot 328 of end effector 330 is disposed in registration (e.g., concentric) with knife 232a of knife assembly 232, and outer treatment surfaces 234 of head 230 of uterine manipulator 200 are in registration (e.g., concentric) with inner treatment surfaces 332a, 334a of end effector 330. In this clamped position, electrical energy can be activated, for example, via actuator 224b to transmit electrosurgical energy (e.g., monopolar, bipolar, or combinations thereof) from energy source 100 through treatment surfaces 234 of head 230 and treatment surfaces 332a, 334a of end effector 330 so that the electrosurgical energy treats the clamped tissue disposed between the respective treatment surfaces 234, 332a, 334a of uterine manipulator 200 and electrosurgical instrument 300.

Figure 14:
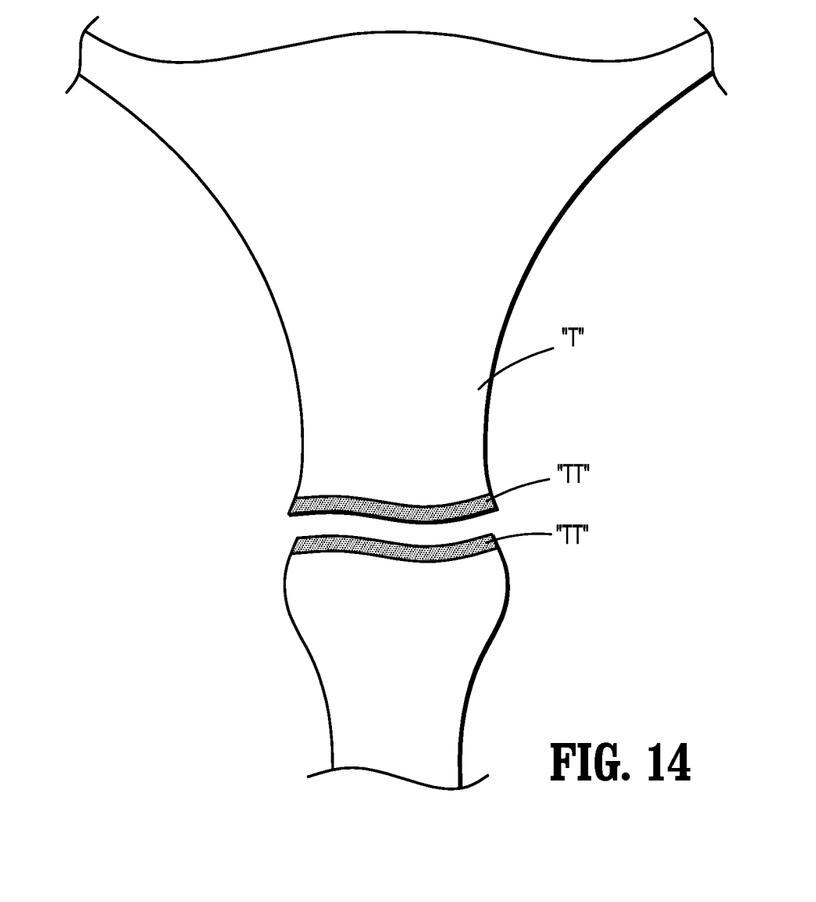

Once the clamped tissue is treated, knife 232a of knife assembly 232 of uterine manipulator 200 can be deployed by actuating actuator 224a (and/or rotatable actuator 222) to retract retractable door 232c so that knife 232a is urged radially outwardly by a bias of spring 232b, as indicated by arrows "B" (see FIGS. 10 and 11), to expose knife 232a for cutting the treated tissue "TT." With knife 232a deployed, rotatable actuator 222 can be rotated (or further rotated), as indicated by arrows "A," to enable knife 232a to travel along arcuate path "AP" through blade slot 328 to make an annular incision (e.g., circular) for severing the treated tissue "TT" to effectuate a colpotomy (see FIG. 14). Uterine manipulator 200 and electrosurgical instrument 300 can then be removed.

Figure 15:
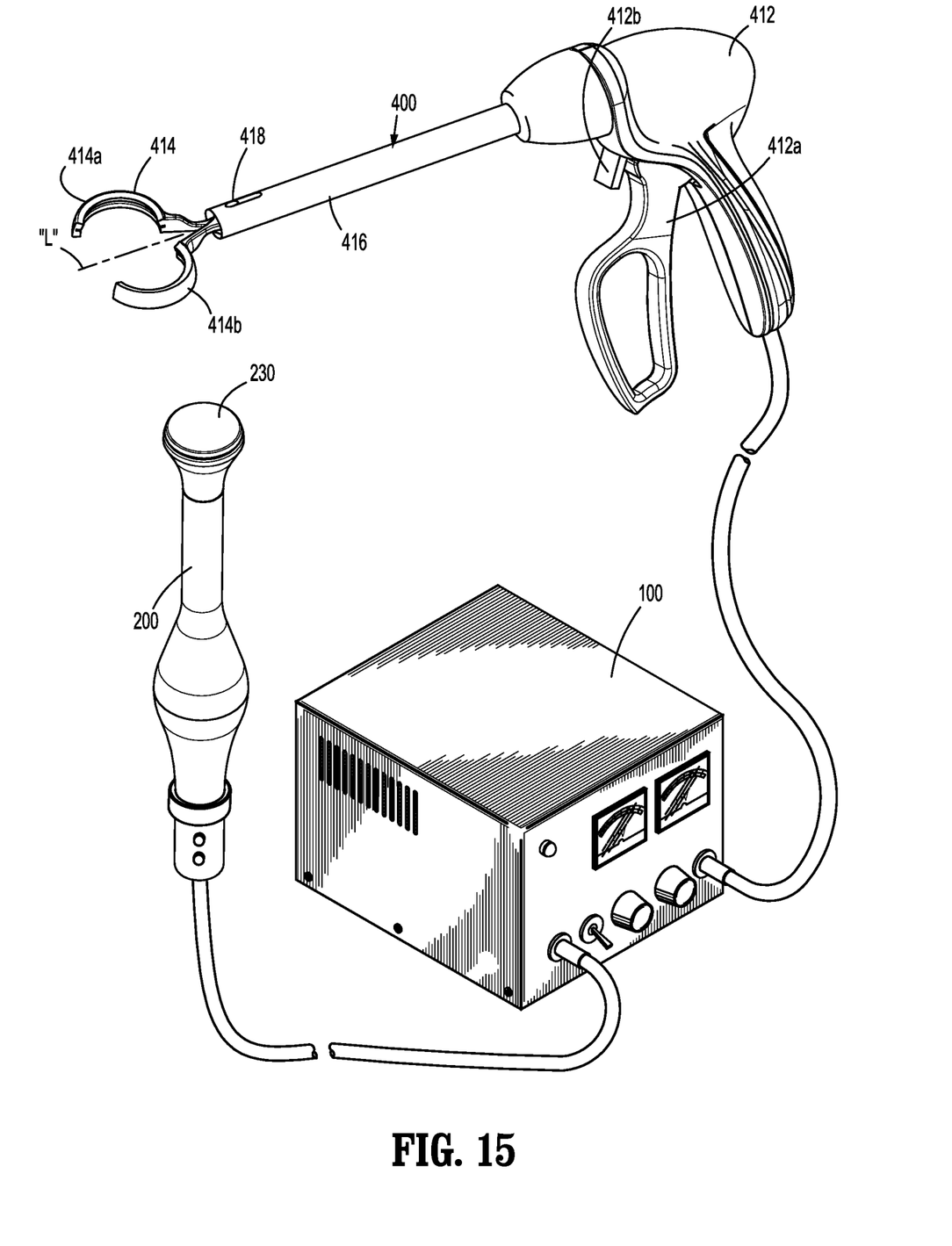
FIG. 15 is a perspective view of another colpotomy system in accordance with the principles of this disclosure.

As seen in FIG. 15, electrosurgical instrument can have a minimally invasive construction and may be in the form of electrosurgical instrument 400. Briefly, electrosurgical instrument 400 defines a longitudinal axis "L" and generally includes an instrument housing 412, an elongated shaft assembly 416 that extends from instrument housing 412, and an end effector 414 supported on a distal end of elongated shaft assembly 416. End effector 414 is similar to end effector 330 and is operable by a drive assembly 418 coupled to instrument housing 412 to pivot first and second jaw members 414a, 414b of end effector 414 between open and closed positions to clamp tissue onto head 230 of uterine manipulator 200 similar to electrosurgical instrument 300. As can be appreciated, drive assembly 418 can include any suitable mechanical, electrical, and/or electromechanical component configured to impart force (e.g., axial, rotational, or combinations thereof) to end effector 414 (e.g., pneumatic, hydraulic, cables, rods, gears, pulleys, circuits, controllers, wiring, etc.).

Instrument housing 412 supports various actuators 412a, 412b for remotely controlling end effector 414 through the elongated shaft assembly 416. Although this configuration is typically associated with instruments for use in laparoscopic or endoscopic surgical procedures, various aspects of this disclosure may be practiced in connection with endoluminal procedures and with traditional open instruments such as electrosurgical instrument 300. For a more detailed description of a similar electrosurgical instruments, or components thereof, which can be included or modified for inclusion in electrosurgical instrument 400, reference can be made, for example, to U.S. Pat. No. 9,655,673 to McCullough, Jr. et al. and U.S. Pat. No. 9,820,765 to Allen et al., incorporated by reference hereinabove.

In aspects, electrosurgical instruments 300, 400 can include one or more actuators (not shown) for activating electrosurgical energy from energy source 100, instead of, or in addition to actuator 224b of uterine manipulator 200. In aspects, a knife assembly can be incorporated into electrosurgical instruments 300, 400, instead of, or in addition to, knife assembly 232 of uterine manipulator 200. In aspects, the disclosed jaw members can be configured to pivot together and/or independent of one another. In aspects, rotatable actuator 222 can be actuated to rotate knife 232a of knife assembly 232 relative to head 230 of uterine manipulator 200, for example, through an annular channel (not shown) defined in the outer side surface of head 230 of uterine manipulator 200. In aspects, colpotomy system 10, or portions thereof, may be single use (e.g., disposable) or reusable. For instance, uterine manipulator 200 or electrosurgical instrument 300 may be configured for a single use. In another example, end effector 414 and/or elongated shaft assembly 416 may be selectively removable from instrument housing 412 for disposal after a single use.

Securement of any of the components of the disclosed devices may be effectuated using known securement techniques such welding, crimping, gluing, fastening, etc.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

For a detailed description of exemplary medical work stations and/or components thereof, reference may be made to U.S. Patent Application Publication No. 2012/0116416, and PCT Application Publication No. WO2016/025132, the entire contents of each of which are incorporated by reference herein.

Persons skilled in the art will understand that the structures and methods specifically described herein and shown in the accompanying figures are non-limiting exemplary aspects, and that the description, disclosure, and figures should be construed merely as exemplary of particular aspects. It is to be understood, therefore, that this disclosure is not limited to the precise aspects described, and that various other changes and modifications may be effectuated by one skilled in the art without departing from the scope or spirit of the disclosure. Additionally, the elements and features shown or described in connection with certain aspects may be combined with the elements and features of certain other aspects without departing from the scope of this disclosure, and that such modifications and variations are also included within the scope of this disclosure. Accordingly, the subject matter of this disclosure is not limited by what has been particularly shown and described.

What is claimed is:

1. An electrosurgical colpotomy system, comprising:
an energy source;
an electrosurgical instrument having a shaft assembly including an end effector supported on a distal end portion of the shaft assembly, the end effector in electrical communication with the energy source, the end effector including a first jaw member and a second jaw member supporting a first treatment surface and movable relative to the first jaw member between an open position and a closed position, the first jaw member having a proximal end and a distal end, the first jaw member defining a first blade slot that extends through the distal end of the first jaw member, and the second jaw member having a proximal end and a distal end, the second jaw member defining a second blade slot that extends through the distal end of the second jaw member, wherein the first and second blade slots align with another to define an annular blade slot through the end effector when the first and second jaw members are disposed in the closed position; and
a uterine manipulator defining a longitudinal axis and having a head including a second treatment surface, the second treatment surface electrically coupled to the energy source and configured to transmit electrical energy to the first treatment surface when the first and second jaw members are positioned about the head of the uterine manipulator, the head supporting a knife assembly having a knife that is configured to rotate through the distal ends of the first and second jaw members as the knife moves about the longitudinal axis and through the annular blade slot of the end effector.

2. The electrosurgical colpotomy system of claim 1, wherein the first and second jaw members of the end effector are selectively movable between the open position and the closed position to capture tissue between the head of the uterine manipulator and the end effector of the electrosurgical instrument.

3. The electrosurgical colpotomy system of claim 1, wherein the first treatment surface includes a first seal plate and the second treatment surface includes a second seal plate, wherein the first seal plate and the second seal plate are configured to conduct electrical energy from the energy source.

4. The electrosurgical colpotomy system of claim 1, wherein the uterine manipulator includes a rotatable actuator that is operable to enable the knife to rotate about the longitudinal axis.

5. The electrosurgical colpotomy system of claim 2, wherein the first jaw member and the second jaw member have an arcuate profile that cooperate to define a ring when the first jaw member and the second jaw member are disposed in the closed position.

6. The electrosurgical colpotomy system of claim 5, wherein the ring is configured to receive the head of the uterine manipulator.

7. The electrosurgical colpotomy system of claim 1, wherein the energy source includes a generator.

8. A colpotomy system, comprising:
a surgical instrument having a shaft assembly, the shaft assembly including an end effector supported on a distal end portion of the shaft assembly, the end effector including a first jaw member and a second jaw member, the first jaw member having a proximal end and a distal end, the first jaw member defining a first blade slot that extends distally through the distal end of the first jaw member, and the second jaw member having a proximal end and a distal end, the second jaw member defining a second blade slot that extends distally through the distal end of the second jaw member; and a uterine manipulator extending distally to a head supporting a knife that is positioned to cooperate with the first and second jaw members of the end effector, the knife configured to rotate through the distal ends of the first and second jaw members as the knife rotates about the head.

9. The colpotomy system of claim 8, wherein the first and second jaw members are selectively movable between an open position and a closed position to capture tissue between the head of the uterine manipulator and the end effector.

10. The colpotomy system of claim 8, wherein the uterine manipulator includes a rotatable actuator operatively coupled to the knife, the rotatable actuator operable to rotate the knife relative to the end effector of the electrosurgical instrument.

11. The colpotomy system of claim 9, wherein the first jaw member and the second jaw member have an arcuate profile that defines a ring when the first jaw member and the second jaw member are disposed in the closed position.

12. The colpotomy system of claim 8, wherein the uterine manipulator and the surgical instrument are coupled to a generator.

* * * * *